(12) United States Patent
Brun et al.

(10) Patent No.: US 8,435,796 B2
(45) Date of Patent: May 7, 2013

(54) USE OF A FABRIC COMPRISING A SPECIFIC MATERIAL FOR DETECTING THE PRESENCE OF A CHEMICAL SUBSTANCE

(75) Inventors: Jean Brun, Champagnier (FR);
Catherine Durand, Saint R Theoffrey (FR); Alain Soubie, Saint Egreve (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 60 days.

(21) Appl. No.: 12/947,725

(22) Filed: Nov. 16, 2010

(65) Prior Publication Data
US 2011/0117663 A1    May 19, 2011

(30) Foreign Application Priority Data

Nov. 17, 2009 (FR) .................................... 09 58112

(51) Int. Cl.
*G01N 33/00* (2006.01)
(52) U.S. Cl.
USPC ........ 436/101; 436/151; 436/902; 422/82.05; 422/91
(58) Field of Classification Search ................ 422/82.05, 422/91
See application file for complete search history.

(56) References Cited

U.S. PATENT DOCUMENTS

| 5,674,752 A | * | 10/1997 | Buckley et al. | ............... | 436/151 |
| 2004/0009726 A1 | | 1/2004 | Axtell et al. | | |
| 2007/0037462 A1 | | 2/2007 | Allen et al. | | |

FOREIGN PATENT DOCUMENTS

| FR | 2 806 164 A1 | 9/2001 |
| GB | 2 208 358 A | 3/1989 |
| JP | 05 154077 A | 6/1993 |
| WO | WO 2005/078432 A2 | 8/2005 |

OTHER PUBLICATIONS

Meoli, D, et al. Interactive electronic textile development: A review of technologies, 2002, Journal of Textile and Apparel, Technology and Management, vol. 2(2), pp. 1-11.*
Coyle, S. et al Textile-based wearable sensors for assisting sports performance, Jun. 3-5, 2009, Wearable and implantable body sensor networks, Sixth International Workshop.*

* cited by examiner

*Primary Examiner* — Robert Xu
(74) *Attorney, Agent, or Firm* — Miles & Stockbridge P.C.

(57) ABSTRACT

A method for using of a fabric comprising a material chosen from metals, metallic alloys, polymers, inorganic compounds and mixtures thereof, which material is capable of detecting the presence of a chemical substance, for the detection of said chemical substance.

18 Claims, No Drawings

USE OF A FABRIC COMPRISING A SPECIFIC MATERIAL FOR DETECTING THE PRESENCE OF A CHEMICAL SUBSTANCE

TECHNICAL FIELD

The present invention relates to the use of a fabric comprising a specific material capable of detecting the presence of a chemical substance, which fabric may enter into the constitution of clothing, for example safety clothing, to detect the presence of a chemical substance, in particular an acid substance.

Thus, the invention finds its application for the detection of chemical substances in contexts where the presence of said substances may be harmful to the body, for example in chemical factories.

The invention may further make it possible to detect the start of an industrial incident, for example the emission of chemical substances following a leak.

The field of the invention is thus that of the detection of chemical substances, in an industrial environment, by textiles constituting clothing worn by persons in contact with such an environment.

BACKGROUND

In the prior art, there exists a certain number of methods intended to detect a chemical substance, particularly when the chemical substance is an acid or a base.

Thus, it has been known for a long time to resort to the technique of pH paper to detect whether a liquid medium contains an acid or a base. This pH paper is soaked with a universal indicator, which is designed to change colour gradually as a function of the pH. This universal indicator conventionally corresponds to a mixture of coloured indicators, each of the coloured indicators of the mixture having one or even two change of colour zones for well determined pH ranges. The coloured indicators are chosen in such a way as to make it possible, thanks to the change of colour that has taken place, to obtain rapidly the pH of a solution, and are also capable of covering pHs ranging from 0 to 14.

Nevertheless, this method of detection stems from a direct wish of the user to detect the presence of a given chemical substance and does not enable the detection of such a substance without the intervention of said user. In other words, the aforementioned method does not enable the unexpected leak of a chemical substance to be spontaneously detected, in an environment where such a leak is prohibited.

To offset this insufficiency, other authors have imagined using the principle of the detection of a chemical substance by coloured indicators by impregnating fabrics with such substances and making, from these fabrics, clothing intended to be worn by users in contact with environments where it is important to detect spontaneously the presence of a chemical substance, for example following a leak of said substance, which could be at the origin of an industrial incident if the problem is not checked.

Thus, the user finding himself, in the context of his activities, in unexpected contact with the undesirable substance, could immediately observe a change of colour of his outfit and thus avert any incident by immediately resolving the problem of the leak of the undesirable substance.

This is the case of clothing conceived from fabrics impregnated with a resin containing a coloured indicator able to change colour in the presence of a given chemical substance, more precisely in the presence of an acid substance.

Nevertheless, this type of embodiment has the following drawbacks:
  the fabrics used do not make it possible to detect precisely the nature of the acid substance, which has entered into contact with them;
  the fabrics used are difficult to upkeep, because the coloured indicators impregnating the fabric may be eliminated in part during washing.

There thus exists a real need for fabrics, which can enter into the constitution of safety clothing, capable of detecting the presence of a chemical substance, which fabrics do not have the drawbacks of those of the prior art.

SUMMARY

Thus, the invention relates to the use of a fabric comprising a material chosen from metals, metallic alloys, polymers, inorganic compounds and mixtures thereof, for the detection of a chemical substance, which material is capable of detecting the presence of said chemical substance by reaction of said chemical substance with said material, said reaction being materialised by a change of colour of said material.

The use of a fabric comprising such a material for the detection of a chemical substance has the following advantages:
  the material present in the fabric for the detection of a chemical substance is resistant to the washing of the fabric;
  the material, by being chosen in an appropriate manner, may enable the detection of a specific chemical substance and thus the identification of said substance.

DETAILED DESCRIPTION

Before entering into greater detail in the description of the invention, the following points are made clear.

Fabric is conventionally taken to mean:
  a woven fabric, in other words a woven material formed by the intertwining of two sets of yarns, generally a set of warp yarns and a set of weft yarns;
  an unwoven fabric, in other words an assembly of fibres, held together by mechanical interlacing (for example, by needling), which gives a veil or a mat, the fibres of which are arranged randomly, by fusion of fibres or by linking of fibres by means of a binding agent; or
  a knitted fabric, in other words a fabric resulting from the interlacing of series of loops formed by one or several yarns.

The fabric may further comprise one or more ribbons associated with yarns and/or fibres.

Yarn is conventionally taken to mean, according to the invention, the continuous strands entering into the constitution of the fabric intended to be interlaced or assembled to give the fabric, a yarn that can be constituted of a single filament (then known as monofilament) with or without torsion, a set of filaments twisted together (then known as thread), or a set of filaments maintained together without torsion (then known as torsion-free yarn). The yarns and/or filaments may have any type of section (for example, a square section, a circular section or a rectangular section).

Ribbon is conventionally taken to mean a piece in which its transversal section assumes, at least approximately, the shape of a long rectangle, this section being substantially the same all along the ribbon.

The fabric used according to the invention for the detection of a chemical substance may result from an association of a set of yarns, which yarns comprise at least one material as defined above, the yarns being able to be entirely constituted of filament(s) comprising said material or filaments comprising said material twisted with filaments not comprising said material, the fabric being able to further comprise one or more ribbons comprising at least one material as defined above. Said fabric may further comprise other yarns and/or other ribbons, namely yarns and/or ribbons not comprising said material, for example, yarns or ribbons made of natural fibre (such as cotton, wool), yarns or ribbons made of synthetic fibre (such as polyamide yarns).

Thus, in a fabric used according to the invention, certain yarns or ribbons may not comprise material capable of detecting the presence of the desired chemical substance and may thus only have a mechanical or decorative function.

The yarns and/or ribbons as defined above (namely, the yarns and/or ribbons comprising said material capable of detecting the desired chemical substance) and probably the other yarns and/or ribbons as defined above may be associated so that, in the presence of the chemical substance to be detected, a pattern appears indicating the presence of said substance, this pattern may, for example, be in the form of a message indicating the nature of the substance detected.

Thus, in the presence of such a substance, the yarns and/or ribbons comprising a material capable of detecting the desired chemical substance are going to react with said substance, which reaction is materialised by a change of colour of said yarns and/or ribbons, which enables the visual appearance of said pattern to the naked eye by contrast with the other yarns and/or ribbons, the colour of which remains unchanged in the presence of said substance.

A method of weaving enabling the formation of patterns in a fabric is the Jacquard weaving method, well known to those skilled in the art.

The material capable of detecting the presence of a chemical substance included in the fabric may be advantageously a metal or metallic alloy, this material being particularly advantageous, in the sense that it is capable of changing colour in the presence of a given chemical substance. Moreover, the fabric comprising such a material may have, further, antistatic properties.

Metal is conventionally taken to mean a metallic element in its 0 oxidation state, such as alkali metals, alkaline-earth metals (for example, Mg), transition metals (for example, Ni, Ti, Cu, Co and Fe), poor metals (for example, Al, Ga, In, Sn, Tl, Pb and Bi), non metallic elements (for example, Si, Ge). In particular, it may be nickel and titanium at 0 oxidation state. Metallic alloy is taken to mean an association of two or more of the aforementioned metals.

The detection of the chemical element by said metal or metallic alloy may take place through reaction of said chemical element with said metal or metallic alloy bringing about a change of colour of the latter, for example by oxidation-reduction reaction. Thus, for example, when the fabric comprises metallic iron, the latter in the presence of a chemical substance is able to oxidise the iron into ferric ions (as it happens, the substance that it is wished to detect) and is going to change colour (passage from a grey colour to a rust colour) thereby attesting to the presence of said substance.

The metal or metallic alloy present in the aforementioned fabric and able to ensure the detection of a given chemical substance may be in one or more of the following forms:

metallic yarns comprising one or more metallic filaments constituted of said aforementioned metal or metallic alloy and probably one or more metallic filaments constituted of another metal or metallic alloy;

metallic or non metallic yarns coated with a layer of aforementioned said metal or metallic alloy, said yarns being able to be obtained by evaporation or cathodic sputtering of said metal or metallic alloy on the aforementioned non metallic or metallic yarns;

yarns, comprising both one or more metallic filaments constituted of said metal or metallic alloy and one or more non metallic filaments (for example, one or more metallic filaments constituted of said metal twisted with one or more non metallic filaments).

The metal or metallic alloy may also be present in the form of a ribbon constituted of said metal or metallic alloy or a ribbon (for example, a ribbon made of polyamide) coated with a layer of said metal or metallic alloy.

The fabric comprising the metal may further comprise non metallic yarns and/or metallic yarns constituted of a metal or metallic alloy not capable of detecting the presence of the desired chemical substance.

The chemical substances capable of being detected by fabrics comprising the metal or a metallic alloy used according to the invention may be of various types.

They may be basic substances, acid substances or instead metallic elements existing probably in the form of oxides or halides.

Thus, by way of examples of metallic elements, iron, which can exist, in solution, in the form of iron halide, such as iron chloride $FeCl_3$, may be cited. This substance may be detected by being placed in contact with a fabric comprising aluminium and/or copper.

Cobalt, which can exist in the form of oxide in aqueous acid solution, such as a solution of sulphuric acid, may also be cited. In such a medium, cobalt may be detected when it enters into contact with a fabric comprising iron, cobalt, copper or nickel.

It may involve acid substances, such as hydrofluoric acid. Indeed, it may be very interesting to detect the presence of hydrofluoric acid in domains where this acid is particularly used, as is the case of microelectronics.

Hydrofluoric acid may be detected by being placed in contact with a fabric comprising titanium.

Thus, according to a first embodiment, this fabric may consist in an entanglement of a first category of yarns each consisting in a ribbon coated with a layer of titanium twisted with one or more filaments made of polyamide and of a second category of yarns each consisting in a ribbon coated with a layer of nickel twisted with one or more filaments made of polyamide.

According to a second embodiment, this fabric may consist in an entanglement of yarns made of copper coated with a layer of titanium and yarns made of stainless steel.

By way of examples, the table below indicates chemical substances capable of being detected by contact with fabrics comprising the elements listed in the right hand column.

| Chemical substance | Metal |
|---|---|
| HCl + $HNO_3$ solution | Nickel |
| HF solution | Ti |
| $H_2O_2$ + $NH_3$ solution | Cu, Ti |
| $H_3PO_4$ solution | Al, Mg |
| $H_2SO_4$ solution | Cr, Fe, Ti |
| NaOH solution | Si |
| KOH solution | Si |
| $HNO_3$ + HF solution | Ge |

The material capable of detecting the presence of a chemical substance included in the fabric may also be an inorganic compound, such as an oxide ceramic, like $Fe_2O_3$, $Al_2O_3$, $SiO_2$.

The chemical substances capable of being detected by fabrics comprising an inorganic compound may be acid substances.

Thus, by way of examples:
- a fabric comprising $Fe_2O_3$ may enable the detection of oxalic acid;
- a fabric comprising $Al_2O_3$ may enable the detection of phosphoric acid, probably in an alcohol solution comprising, for example, isopropyl alcohol;
- a fabric comprising $SiO_2$ may enable the detection of hydrofluoric acid.

The material capable of detecting the presence of a chemical substance included in the fabric may also be a polymer, such as a polyamide or a polyester such as polyethylene terephthalate (known by the abbreviation PET).

By way of example, a fabric comprising PET may enable the presence of nitric acid to be detected.

The aforementioned fabrics may enter into the constitution of clothing, for example safety clothing, the consignees of which are caused to work in environments where it is necessary to detect the presence of a chemical substance, this presence being able to indicate a leak of said substance, that is thus able to lead to, if not checked, an industrial incident.

The invention will now be described with reference to the following examples, given by way of non-limiting illustration.

Example

This example illustrates the use of a specific fabric for the detection of hydrofluoric acid.

This fabric is obtained by weaving of two categories of yarns:
- a first category of yarns, of which each of the yarns consists in a ribbon made of PET (PET signifying polyethylene terephthalate), for example 500 μm wide by 50 μm thick coated with a layer of titanium 1000 Å thick twisted with filaments made of polyamide;
- a second category of yarns, of which each of the yarns consists in a ribbon of PET 500 μm wide by 50 μm thick coated with a layer of nickel 1000 Å thick twisted with filaments made of polyamide.

The fabric obtained from the weaving of these two categories of yarns has a uniform colour.

When the fabric is placed in the presence of hydrofluoric acid, only the yarns comprising a titanium based ribbon change colour, the fabric thus no longer having visually a uniformity of colour.

The same type of result may be obtained with a fabric obtained by weaving yarns made of copper coated with a layer of titanium and yarns made of stainless steel, only the yarns made of copper coated with a layer of titanium reacting and indicating the presence of hydrofluoric acid.

This fabric may thus be used to make safety clothing intended to be worn by users working in environments where leaks or splashes of hydrofluoric acid are possible, which is the case of microelectronics laboratories.

We claim:

1. A method for the detection of a chemical substance, comprising:
    reacting said chemical substance with a material in a fabric, wherein said material is chosen from among metals, metallic alloys, polymers, inorganic compounds and mixtures thereof,
    wherein said material is capable of detecting the presence of said chemical substance, and
    wherein said reacting is materialised by a change of colour of said material.

2. The method according to claim 1,
    wherein the fabric is an association of a set of first yarns comprising at least one material as defined in claim 1,
    wherein said set of first yarns is constituted of one or more filaments comprising said material, and
    wherein the fabric further comprises one or more first ribbons comprising at least one material as defined in claim 1.

3. The method according to claim 2, wherein the fabric further comprises second yarns or second ribbons not comprising a material as defined in claim 1.

4. The method according to claim 3,
    wherein the first and second yarns and the first and second ribbons are configured so that, in the presence of the chemical substance to be detected, a pattern is generated indicating the presence of said substance.

5. The method according to claim 1, wherein the material is a metal or a metallic alloy.

6. The method according to claim 5,
    wherein the metal or metallic alloy is present in the fabric in the form of one or more of
        metallic yarns comprising one or more metallic filaments constituted of said metal or metallic alloy and one or more metallic filaments constituted of another metal or metallic alloy;
        metallic or non-metallic yarns coated with a layer of said metal or metallic alloy;
        yarns comprising one or more metallic filaments constituted of said metal or metallic alloy and one or more non-metallic filaments; and
        a ribbon constituted of said metal or metallic alloy or a ribbon coated with a layer of said metal or metallic alloy.

7. The method according to claim 5,
    wherein the fabric further comprises second yarns constituted of a metal or metallic alloy not capable of detecting the presence of said chemical substance.

8. The method according to claim 1, wherein the chemical substance to be detected is an acid substance.

9. The method according to claim 8, wherein the acid substance is hydrofluoric acid.

10. The method according to claim 9, wherein the fabric capable of detecting hydrofluoric acid is a fabric comprising titanium.

11. The method according to claim 1,
    wherein the fabric comprises an entanglement of a first category of yarns each having a ribbon coated with a layer of titanium twisted with one or more filaments made of polyamide, and a second category of yarns each having a ribbon coated with a layer of nickel twisted with one or more filaments made of polyamide.

12. The method according to claim 1,
    wherein the fabric comprises an entanglement of yarns made of copper coated with a layer of titanium, and yarns made of stainless steel.

13. The method according to claim 1, wherein the inorganic compound is an oxide ceramic.

14. The method according to claim 1, wherein the polymer is a polyamide or a polyester.

15. The method according to claim 1, wherein the fabric is a component of a safety clothing.

16. The method according to claim 1,
    wherein the fabric is an association of a set of first yarns comprising at least one material as defined in claim 1, wherein said set of first yarns is constituted of one or more filaments comprising said material twisted with filaments not comprising said material, and wherein the fabric further comprises one or more first ribbons comprising at least one material as defined in claim 1.

17. The method according to claim 16, wherein the fabric further comprises second yarns or second ribbons not comprising a material as defined in claim 1.

18. The method according to claim 17, wherein the first and second yarns and the first and second ribbons are configured so that, in the presence of the chemical substance to be detected, a pattern is generated indicating the presence of said substance.

* * * * *